United States Patent

Botta

[11] 4,003,907
[45] Jan. 18, 1977

[54] Δ¹-1-AZACYCLOALKENE-2-CARBOXYLIC ACIDS AND THEIR PRODUCTION

[75] Inventor: Artur Botta, Krefeld, Germany

[73] Assignee: Bayer Aktiengesellschaft, Germany

[22] Filed: Nov. 27, 1974

[21] Appl. No.: 527,582

[30] Foreign Application Priority Data
Dec. 1, 1973 Germany .......................... 2359990

[52] U.S. Cl. ..................... 260/295 R; 260/239 BE; 260/326.2

[51] Int. Cl.² ............ C07D 207/02; C07D 211/08; C07D 223/04

[58] Field of Search ....... 260/295 R, 239 BE, 326.2

[56] References Cited
OTHER PUBLICATIONS

Chemical Abstracts 75:21427h (1971).
Vinnik et al., Chemical Abstracts 60:387b (1964).
Macholan et al., Chemical Abstracts 58: 11465b (1963).
Beer et al., Chemical Abstracts 63: 1709a (1965).
Kyowa, Chemical Abstracts 72: 90303q (1970).
Hasse, Chemical Abstracts 60: 15824g (1964).

*Primary Examiner*—Norman A. Drezin

[57] ABSTRACT

A compound of the formula

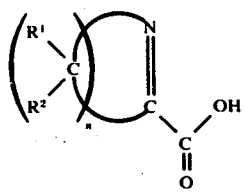

(I).

or a salt thereof,
or of the formula

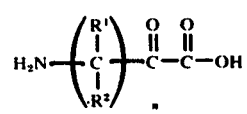

(Ia).

or a salt thereof, wherein
R¹ and R² are the same or different and each is hydrogen, lower alkyl, cycloalkyl of 4 to 7 carbon atoms, aryl of 6 to 14 carbon atoms, or aralkyl of up to 18 carbon atoms wherein the alkyl moiety contains up to 6 carbon atoms; and
n is 3, 4 or 5;
is produced by hydrolyzing a compound of the formula

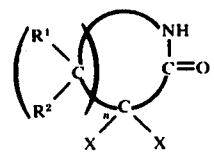

(II).

wherein
R¹, R² and n are as above defined, and
X is halogen;
a compound of the formula

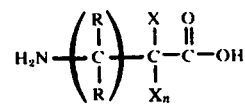

(III).

or a hydrohalide thereof, wherein
R¹, R², n and X are as above defined; or
a compound of the formula

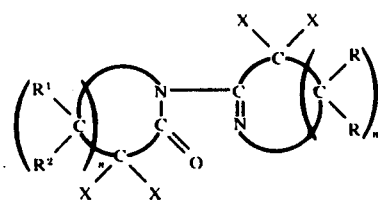

(IV)

wherein
R¹, R², n and X are as above defined;
in the presence of a base at a temperature of from about 20° to about 180° C.

The compounds produced are valuable intermediates from which cyclic amino acids and α,ω-diaminocarboxylic acids are obtained.

13 Claims, No Drawings

Δ¹-1-AZACYCLOALKENE-2-CARBOXYLIC ACIDS AND THEIR PRODUCTION

The present invention relates to a process for the production of Δ¹-1-azacycloalkene-2-carboxylic acids and salts thereof from compounds containing a 2,2-dihalogenolactam ring configuration.

More particularly, the present invention is concerned with a process for the production of Δ¹-1-azacycloalkene-2-carboxylic acids of the formula

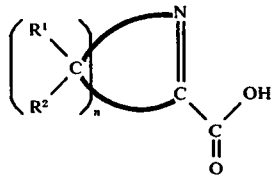         (I), or a salt thereof, or of the formula

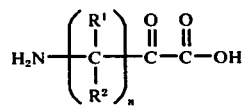         (Ia), or a salt thereof, wherein
R¹ and R² are the same or different and each is hydrogen, lower alkyl, cycloalkyl preferably of 4 to 7 carbon atoms, aryl preferably of 6 to 14 carbon atoms, or aralkyl preferably of up to 18 carbon atoms of which preferably up to 6 carbon atoms are in the alkyl moiety and
n is 3, 4 or 5,
which comprises hydrolyzing a 2,2-dihalogenolactam of the formula

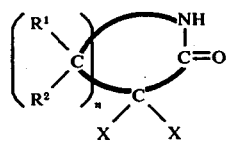         (II), wherein
R¹, R² and n are as above defined, and
X is halogen,
the corresponding ω-amino-2,2-dihalogenocarboxylic acid of the formula

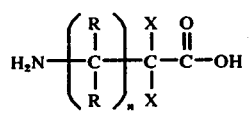         (III), or a hydrohalide thereof, wherein
R¹, R² n and X are as above defined,
or the corresponding anhydro-di-2,2-dihalogenolactam of the formula

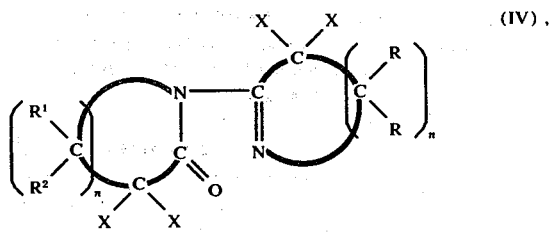         (IV), wherein
R¹, R², n and X are as above defined,
in the presence of a base.

Where R¹ and R² are indicated above as being either the same or different, it is meant that R¹ can be the same as or different from R² and also that each R¹ and each R² on each carbon atom can be the same or different from each other R¹ and each other R².

Preferably, n is 3 or 4.

The process of the present invention is preferably carried out at a temperature of from about 20° to about 180° C, and particularly in the range of 50° to 120° C, and especially in the range of about 80° to about 110° C.

The preferred lower alkyl moieties include both straight and branched chain alkyl moieties of 1 to 6 carbon atoms such as methyl, ethyl, propyl, isopropyl, butyl, isobutyl, tert.-butyl, amyl, isoamyl, as well as the other isomeric pentyl moieties as well as hexyl and the isomeric hexyl moieties.

The especially preferred alkyl moieties are those of 1 to 4 carbon atoms.

The preferred cycloalkyl moiety is the cyclohexyl moiety.

The preferred aryl moieties are phenyl and naphthyl.

The preferred aralkyl moieties are those wherein the aryl moiety is phenyl and the alkyl moiety is of 1 to 3 carbon atoms. The benzyl moiety is an especially preferred aralkyl moiety.

The preferred halogens are chlorine and bromine.

Formula Ia represents compounds which, depending on the pH value, can be in a hydrolytic equilibrium in aqueous solution with compounds of the formula I above. Additionally, when R² on the carbon atom adjacent to the doubly-bonded carbon atom is hydrogen, compounds of the formula I exist in tautomeric form Ib:

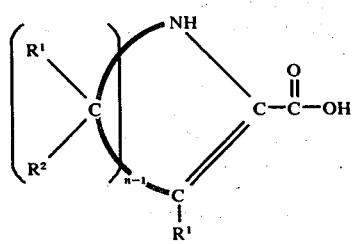         (Ib), wherein
R¹, R² and n are as above defined.

For example, Δ¹-pyrroline-2-carboxylic acid at low pH values is preferably in the open-chain form (Ia) while at higher pH values it corresponds to the cyclic form (I); on the other hand, Δ¹-tetrahyropicolinic acid predominantly corresponds to the cyclic form (I) and, in accordance with the form (I), at low pH values in aqueous solution, is predominantly present as a cation through taking up a proton on the nitrogen, while at higher pH values it is predominantly present in the form (Ib) as the carboxylate anion (compare Chem. Ber. 96, 237–46 (1963)).

The free $\Delta^1$-azacycloalkene-2-carboxylic acids of the formula I, such as, for example, $\Delta^1$-tetrahydropicolinic acid, are, in part, not stable, especially in solution (Biochem. J. 105, 663–667 (1967)). It is therefore desirable to isolate and store them in the form of their metal salts or acid addition salts.

2,2-Halolactams which can be used as starting products, in the process according to the invention are known or can be prepared according to known processes, [Compare U.S. Pat. Nos. 2,832,769; 2,836,592; BE-PS No. 609,822; JA-PS No. 69/29,455; C.A. 58, 13,917e–g (1963); C.A. 45, 2469c (1951). J. Heterocycl. Chem. (1970) 7 (1) 221–2.]

Derivatives of the following lactams, dihalogenated in the 2,2-position, are representative of starting compounds which are used in the process of the present invention:

5-valerolactam, 5-methyl-5-valerolactam, 4,5- and 5,5-dimethyl-5-valerolactam, 5-ethyl-4-methyl-5-valerolactam, 3-cyclohexyl-5-valerolactam, 3-phenyl-5-valerolactam, 3,4-dihydroquinolone-2, octahydroquinolone-2, 6-caprolactam, the 3- to 6-methyl-6-caprolactams, 6-ethyl-6-caprolactam, 3-isopropyl-6-caprolactam, 4-butyl-6-caprolactam, 4-tert.-butyl-6-caprolactam, 4-isopentyl-6-caprolactam, 4-hexyl-6-caprolactam, 4-cyclohexyl-6-caprolactam, 4-benzyl-6-caprolactam, 4-phenyl-6-caprolactam, 2-oxo-5,6-benz-tetrahydroazepine, 2-oxo-decahydrobenzazepine and 7-oenantholactam.

Further starting compounds which can be used in the process according to the present invention are the ω-amino-2,2-dihalogenocarboxylic acids corresponding to the 2,2-dihalolactams of the formula II, of the formula III and their salts with hydrogen halide acids, and the corresponding anhydrodi-(2,2-dihalo)-lactams of the formula IV.

The compounds of the formulae II and IV are known or can be prepared according to known processes. [Compare Chem. Ber. 63B, 498–502 (1930) or J. Prakt. Chem. 311, 457 (1969).] For example, the compounds III can be obtained by acid hydrolysis of 2,2-dihalolactams II.

The following bases are representative of those which can be used according to the process of the present invention: oxides, hydroxides, carbonates and bicarbonates of alkali and alkaline earth metals, preferably the oxides, hydroxides and carbonates of lithium, sodium, potassium, magnesium, calcium, strontium and barium. Particularly preferred are sodium hydroxide, potassium hydroxide, calcium hydroxide and ammonia and quaternary ammonium hydroxides such as tetramethylammonium hydroxide, tetraethylamonium hydroxide and triethylbenzylammonium hydroxide.

Generally, at least two equivalents of base are used per mol of starting compound. Advantageously, an excess up to 5, and particularly up to 3, equivalents of base per mol of starting compound can be used but a greater excess is not critical.

In general, the process according to the present invention is carried out using a solvent. The following are preferred solvents: water and lower aliphatic alcohols, such as methanol, ethanol, propanol, isopropanol, butanol, isobutanol and tert.-butanol, but also longer-chain alcohols such as isooctanol; alcohols with further functional groups, such as dihydroxydiethyl ether, methylglycol and triethanolamine can also be used; phenols, such as phenol, cresol and xylenols; acid amides, such as dimethylformamide, diethylformamide, dialkylacetamides and N-methylpyrrolidone; ethers such as tetrahydrofurane and dioxane; sulphoxides, such as dimethylsulphoxide.

Of course, solvent mixtures, in particular mixtures of the above-mentioned solvents with one another, can also be used. Aqueous solvent mixtures are used preferentially.

It can also be advantageous to add to the solvent or solvent mixture a commercially available wetting agent, for example, a naphthalenesulphonate or a sodium salt of a sulphuric acid ester. This can be of particular advantage when using water or aqueous solvents, especially if the base used is completely or partially insoluble in water.

The conditions of carrying out the process according to the present invention are not critical. The process can be carried out under normal pressure, under reduced pressure or under elevated pressure.

For example, it is possible to dissolve and/or suspend the 2,2-dihalogenolactam together with the base used in the chosen solvent or solvent mixture, optionally using a wetting agent, bring the reaction mixture to the selected reaction temperature and maintain the latter until the reaction is complete. It is however, also possible to introduce into a solution and/or suspension of the selected base, which is kept at the reaction temperature, the 2,2-dihalogenolactam in bulk or dissolved and/or suspended in the same or in another solvent, all at once, discontinuously or continuously, and after completion of the addition to maintain the reaction temperature until the reaction has ended.

The working up of the resulting reaction mixture can be carried out in the usual manner and is suitably varied in accordance with the chosen solvent and the chosen base. Thus the salts of hydrogen halide acids which are formed as by-products can be soluble in the reaction medium, for example, soluble in water, and can then, for example, be removed advantageously by using ion exchangers. If the above-mentioned salts are insoluble in the reaction medium, they can be separated off according to known methods such as filtration or centrifuging. The same methods can be employed if, conversely, the reaction product is insoluble in the reaction medium and the above-mentioned salts are soluble. A particularly advantageous method for isolating the desired reaction product from a reaction mixture which does not contain any insoluble constituents is to isolate the $\Delta^1$-1-azacycloalkene-2-carboxylic acid formed as a sparingly soluble metal salt or sparingly soluble acid addition salt or, in particular, as a sparingly soluble copper complex salt.

Isolating the reaction product as a sparingly soluble salt is advantageous particularly in cases where the free $\Delta^1$-azacycloalkene-2-carboxylic acids are unstable, as has been mentioned, and can undergo irreversible secondary reactions.

The salts obtained can be purified according to techniques per se known, for example, by recrystallization.

Similarly, the free acid can be obtained from the salts in accordance with techniques per se known; for example, by treating their aqueous solution with anion exchangers or cation exchangers (GB-PS No. 1,176,198), or from the copper complex by precipitating the copper as copper sulphide. Similarly, the copper salt can, for example, be converted into the sodium salt by precipitating the copper with sodium sulphide. The free acid or the salt can be isolated from the solutions thus obtained by stripping off the solvent, if appropriate, in vacuo.

Other known methods of purification and isolation can also be used; for example, chromatographic methods, freeze-drying and molecular-path distillation.

The process according to the present invention can be carried out either batchwise or continuously. It can also be advantageous to carry it out only partially continuously; for example, the reaction according to the present invention can be carried out continuously and the working up of the reaction mixture can be carried out batchwise.

The process according to the invention is illustrated, for the example of 2,2-dichlorocaprolactam, by the equation which follows:

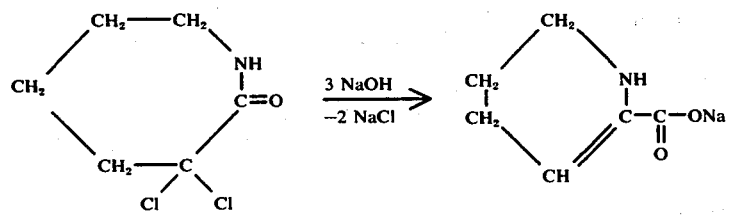

The process according to the present invention is particularly surprising since the acid hydrolysis of 2,2-dichlorocaprolactam leads to ring scission and to the hydrochloride of 6-amino-2,2-dichlorocarboxylic acid. [U.S. Pat. No. 3,163,672; J. Prakt. Chem. (1969) 311, 445–62; J. Am. Chem. Soc. 80, 6233–37 (1958).]

The advantages of the process according to the present invention are several: The starting compounds are obtainable from easily accessible lactams; the bases used are equally easily accessible basic chemicals; and the process according to the present invention is also simple and inexpensive to carry out.

The $\Delta^1$-1-azacycloalkene-2-carboxylic acids of formula I are valuable intermediates. [See British Patent No. 1,176,198.] By catalytic hydrogenation of said compounds the corresponding cyclic amino acids are obtained. On the other hand, if the compounds are reductively aminated, the corresponding $\alpha,\omega$-diaminocarboxylic acids are obtained which are valuable essential amino acids.

Additionally, the cobalt salts of $\Delta^1$-1-azacycloalkene-2-carboxylic acids can be used as accelerators in the peroxide curing of unsaturated polyesters and as driers in air-drying alkyd resins. [Compare Kunstoffhandbuch (Plastics Handbook), Volume VIII, "Polyesters," page 336, Munich 1973; and "Chemistry and Processing of Alkyd Resins," Monsanto Chemical Company, 1952.]

The process of the present invention is more particularly illustrated by the following non-limitative examples.

EXAMPLE 1

364 g (2 mols) of 2,2-dichlorocaprolactam are introduced into a solution of 240 g (6 mols) of sodium hydroxide in 1,500 ml of water and the mixture is heated under nitrogen while stirring, during which the crystals gradually dissolve, and is kept at 100° C for 60 minutes. A solution of 250 g (1 mol) of $CuSO_4.5H_2O$ in 500 ml of water is then allowed to run into the reaction mixture and the solution is filtered while still hot. After cooling, filtering off the product and drying it in air, 260 g (56.6% of theory) of blue crystals of copper $\Delta^1$-tetrahydropicolinate octahydrate, $Cu(C_6H_8NO_2)_2.8H_2O$, are obtained.

EXAMPLE 2

47.5 g (0.2 mol) of 6-amino-2,2-dichlorocaproic acid hydrochloride are introduced into a solution of 32 g (0.8 mol) of sodium hydroxide in 300 ml of water, and the mixture is brought to the reflux temperature under nitrogen while stirring and is kept at 100° C for 40 minutes. A solution of 25 g (0.1 mol) of $CuSO_4.5H_2O$ in 50 ml of water is then added, the solution is filtered while still hot and after cooling the blue crystals which have precipitated are filtered off. This gives 28 g (60.8% of theory) of copper $\Delta^1$-tetrahydropicolinate octahydrate, which is identical with that obtained according to Example 1.

EXAMPLE 3

A solution of 24 g (0.6 mol) of sodium hydroxide in 300 ml of water is brought to 70° C, 33.6 g (0.2 mol) of 2,2-dichloropiperidone are added while stirring and the mixture is then heated to the reflux temperature under nitrogen and is kept at 100° C for 45 minutes. A solution of 25 g (0.1 mol) of $CuSO_4.5H_2O$ in 50 ml of water is then allowed to run into the reaction solution, the mixture is filtered while still hot and after cooling the blue flakes of copper $\Delta^1$-pyrroline-2-carboxylate octahydrate are filtered off: $Cu(C_5H_6NO_2)_2.8H_2O$. The yield is 31 g (71.8% of theory).

EXAMPLE 4

27.1 g (0.1 mol) of 2,2-dibromocaprolactam are added to a solution of 12 g (0.3 mol) of sodium hydroxide in 300 ml of water while stirring at the reflux temperature, under nitrogen, the mixture is kept refluxing for a further 2 hours while stirring, and a solution of 12.5 g (0.05 mol) of $CuSO_4.5H_2O$ in 30 ml of water is then allowed to run into the reaction mixture. After cooling, the blue crystals which have formed are filtered off. The yield of copper $\Delta^1$-tetrahydropicolinate octahydrate is 8 g (34.8% of theory).

EXAMPLE 5

A solution of 32 g (0.8 mol) of sodium hydroxide in 300 ml of water is heated to 80° C, 36.4 g (0.2 mol) of 2,2-dichlorocaprolactam are introduced while stirring under nitrogen, and the reaction mixture is heated to the boil and is kept thereat for 45 minutes. A solution of 25 g (0.1 mol) of $CuSO_4.5H_2O$ and 20 g of concentrated aqueous hydrochloric acid in 50 ml of water is then allowed to run into the reaction solution and after cooling the blue crystals of copper $\Delta^1$-tetrahydropicolinate octahydrate which have formed are filtered off. The yield is 27.5 g (59.8% of theory).

EXAMPLE 6

A solution of 24 g (0.6 mol) of NaOH in a mixture of 150 ml of water and 150 ml of dimethylsulphoxide is heated to 100° C under nitrogen, 36.5 g of 2,2-dichlorocaprolactam are introduced while stirring and the reaction mixture is heated to 115° C for 1 hour. Thereafter, a solution of 25 g (0.1 mol) of $CuSO_4.5H_2O$ in 50 ml of water is added, the mixture is allowed to cool and the crystals of copper $\Delta^1$-tetrahydropicolinate octahydrate which have formed are filtered off. The yield is 27 g (58.7% of theory).

EXAMPLE 7

182 g (1 mol) of 2,2-dichlorocaprolactam are stirred into a solution of 168 g (3 mols) of KOH in 1,500 ml of water under nitrogen at 90° C and the reaction mixture is heated to the boil and is kept at the boil for a further 60 minutes. A solution of 125 g (0.5 mol) of $CuSO_4.5H_2O$ in 250 ml of water is then allowed to run in, the mixture is cooled and the blue crystals of copper $\Delta^1$-tetrahydropicolinate octahydrate which have formed are filtered off. The yield is 134 g (58.3% of theory).

EXAMPLE 8

A solution of 12 g (0.3 mol) of NaOH in 500 ml of water is heated to 80° C, 23.8 g (0.1 mol) of 2,2-dichloro-4-tert.-butyl-caprolactam are stirred in under nitrogen, and heating is continued until the mixture reaches the boil, at which it is kept for 1½ hours. A solution of 12.5 g (0.05 mol) of $CuSO_4.5H_2O$ in 30 ml of water is then poured in and after cooling the blue-grey crystals which have formed are filtered off and recrystallized from 3 parts of methanol. The yield of copper $\Delta^1$-4-tert.-butyl-tetrahydropicolinate ($Cu(C_{10}H_{16}NO_2)_2$) is 15 g (70% of theory): melting point, with decomposition: 260° C.

EXAMPLE 9

19.6 g (0.1 mol) of 2,2-dichloro-oenantholactam are introduced into a solution of 16 g (0.4 mol) of NaOH in 300 ml of water at 100° C while stirring under nitrogen, the mixture is kept at the boil for a further 1½ hours and a solution of 12.5 g (0.05 mol) of $CuSO_4.5H_2O$ and 5 g of concentrated HCl in 50 ml of water is then added. After cooling, the blue crystals which have precipitated even while the mixture was still hot are filtered off and recrystallized from 3 parts of methanol. This gives 11.5 g (67% of theory) of copper $\Delta^1$-tetrahydroazepine-2-carboxylate ($Cu(C_7H_{10}NO_2)_2$), blue crystals of decomposition point 210° C.

EXAMPLE 10

A suspension, at approx. 80° C, of 460 g (1 mol) of copper $\Delta^1$-tetrahydropicolinate octahydrate in 2,000 ml of water is poured into a solution of 240 g (1 mol) of $Na_2S.9H_2O$ in 800 ml of water while stirring under nitrogen, and the suspension, which soon turns black, is stirred further for 30 minutes at 65° C. The copper sulphide formed is then filtered off, the filtrate is concentrated to dryness under a water pump vacuum and the residue is recrystallized from 6 parts of methanol. This gives 251 g (84.2% of theory) of sodium $\Delta^1$-tetrahydropicolinate ($C_6H_8NNaO_2$) as yellow-brownish crystals of melting point 265° C, with decomposition.

What is claimed:

1. The process which comprises treating the lactam of a ω-amino-2,2-dihalocarboxylic acid, said lactam having from 6 to 8 lactam ring members, with at least two molar equivalents of a base selected from the group consisting of (a) an oxide, hydroxide or carbonate of lithium, sodium, potassium, magnesium, calcium, strontium or barium, (b) ammonium hydroxide and (c) a quaternary ammonium hydroxide at temperatures of from about 20° to about 180° C to produce a 1-azacycloalk-1-ene-2-carboxylic acid having one less ring member than said lactam.

2. The process according to claim 1 wherein said lactam has 7 ring members and said 1-azacycloalk-1-ene-2-carboxylic acid has 6 ring members.

3. The process according to claim 1 wherein the ω-amino-2-2-dihalocarboxylic acid is a ω-amino-2,2-dichlorocarboxylic acid or ω-amino-2,2-dibromocarboxylic acid.

4. The process according to claim 3 including the step of converting said 1-azacycloalk-1-ene-2-carboxylic acid into a metal salt.

5. The process according to claim 4 wherein the metal salt is the copper salt.

6. The process according to claim 1 wherein the reaction temperature is from about 50° to about 120° C.

7. The process according to claim 1 wherein the reaction temperature is from about 80° to about 110° C.

8. The process according to claim 1 wherein the base is sodium hydroxide, potassium hydroxide, calcium hydroxide, tetramethylammonium hydroxide, tetraethylammonium hydroxide, or triethylbenzylammonium hydroxide.

9. The process according to claim 1 wherein said treatment is conducted in the presence of water or an inert organic solvent.

10. The process according to claim 9 wherein said treatment is conducted in the presence of a wetting agent.

11. The process according to claim 1 wherein said lactam is the 2,2-dichloro or 2,2-dibromo derivative of a lactam selected from the group consisting of 6-caprolactam, the 3- to 6-methyl-6-caprolactams, 6-ethyl-6-caprolactam, 3-isopropylcaprolactam, 4-butyl-6-caprolactam, 4-tert.-butyl-6-caprolactam, 4-isopentyl-6-caprolactam, 4-hexyl-6-caprolactam, 4-cyclohexyl-6-caprolactam, 4-benzyl-6-caprolactam, 4-phenyl-6-caprolactam, 2-oxo-5,6-benztetrahydroazepine and 2-oxo-decahydrobenzazepine.

12. The process according to claim 1 wherein said lactam is 2,2-dichlorocaprolactam.

13. The process according to claim 1 wherein said lactam is 2,2-dibromocaprolactam.

* * * * *